United States Patent
Lauchard et al.

(10) Patent No.: US 8,088,096 B2
(45) Date of Patent: Jan. 3, 2012

(54) INJECTION DEVICE WITH A CAPACITIVE PROXIMITY SENSOR

(75) Inventors: Gerhard Lauchard, Silberegg (AT); Martin Reindl, Rainbach (AT); Claudia-Carolin Guggenberger, Klagenfurt (AT)

(73) Assignee: Ares Trading S.A., Aubonne (CH)

( * ) Notice: Subject to any disclaimer, the term of this patent is extended or adjusted under 35 U.S.C. 154(b) by 520 days.

(21) Appl. No.: 12/162,052

(22) PCT Filed: Jan. 30, 2007

(86) PCT No.: PCT/IB2007/000199
§ 371 (c)(1),
(2), (4) Date: Jan. 22, 2009

(87) PCT Pub. No.: WO2007/088444
PCT Pub. Date: Aug. 9, 2007

(65) Prior Publication Data
US 2009/0216182 A1     Aug. 27, 2009

Related U.S. Application Data

(60) Provisional application No. 60/833,703, filed on Jul. 27, 2006.

(30) Foreign Application Priority Data

Jan. 31, 2006  (EP) .................................... 06001928

(51) Int. Cl.
*A61M 31/00* (2006.01)
(52) U.S. Cl. ............................ 604/66; 604/131; 604/65
(58) Field of Classification Search .............. 604/65–67, 604/151, 31, 131
See application file for complete search history.

(56) References Cited

U.S. PATENT DOCUMENTS

| | | |
|---|---|---|
| 4,136,291 A | 1/1979 | Waldron |
| 4,766,368 A | 8/1988 | Cox |
| 6,171,276 B1 | 1/2001 | Lippe et al. |
| 6,249,130 B1 | 6/2001 | Greer |
| 6,547,755 B1 * | 4/2003 | Himbert et al. .................. 604/67 |
| 2002/0133113 A1 * | 9/2002 | Madsen et al. .................. 604/65 |

FOREIGN PATENT DOCUMENTS

WO    2005/077441 A2    8/2005

OTHER PUBLICATIONS

International Search Report, Application No. PCT/IB2007/000199, dated Jun. 26, 2007.

* cited by examiner

*Primary Examiner* — Nicholas D Lucchesi
*Assistant Examiner* — Melissa A Snyder
(74) *Attorney, Agent, or Firm* — Nixon Peabody LLP

(57) ABSTRACT

An injection device for injecting medication to a patient, comprising a surface (5) having a through hole (3) for passage of a needle, is characterised by further comprising a capacitive proximity sensor (12, 13, 30) for detecting proximity or contact of human skin to/with said surface (5).

22 Claims, 2 Drawing Sheets

INJECTION DEVICE WITH A CAPACITIVE PROXIMITY SENSOR

The present application is a National Phase of International Application No. PCT/IB2007/000199 filed Jan. 30, 2007 and claims priority to European Patent Application No. 06001928.8 filed Jan. 31, 2006 and U.S. Provisional Patent Application No. 60/833,703 filed Jul. 27, 2006. The contents of all of these applications are expressly incorporated herein by reference in their entireties.

The present invention pertains to an injection device, i.e. to a device for injecting medication to a patient.

Injection devices generally comprise a surface for contacting the patient's skin, which surface has a through hole for passage of a needle connected to a medication container inside the device.

One purpose of the invention is to increase the security of use and handling of an injection device.

To this end there is provided an injection device for injecting medication to a patient, comprising a surface having a through hole for passage of a needle, characterised by further comprising a capacitive proximity sensor for detecting proximity or contact of human skin to/with said surface.

The capacitive sensor is preferably so set that a mere contact of a finger on said surface is not detected and/or that materials such as dry clothes, dry cotton, dry leather, wood, plastic, metal, ceramic, glass are not detected.

The injection device may include a control unit which allows injection of medication only when detection by the sensor occurs. With the above particular setting of the sensor, detection will occur and injection will be allowed only when the device is properly placed on a sufficiently large naked human body area, i.e. typically the body area, such as an arm, where injection should take place. Risks of accidental expelling of medication are therefore reduced.

The injection device may further include a mechanism for moving the needle between a retracted position, inside the device, and an operating position, in which the needle protrudes from the through hole. Preferably, the control unit allows the mechanism to move the needle from the retracted position to the operating position only when detection by the sensor occurs. Such a feature, combined with the above-mentioned setting of the sensor, prevents the needle from being moved out to its operating position while the injection device rests on a hard surface such as a table surface, which could break the needle and injure the user. Such a feature also reduces the risks that the user's skin may be accidentally pierced by the needle when the user is handling the injection device.

More particular embodiments of the injection device according to the invention are defined in the appended dependent claims.

Other features and advantages of the present invention will be apparent from the reading of the following detailed description made with reference to the appended drawings in which.

Figure 1:
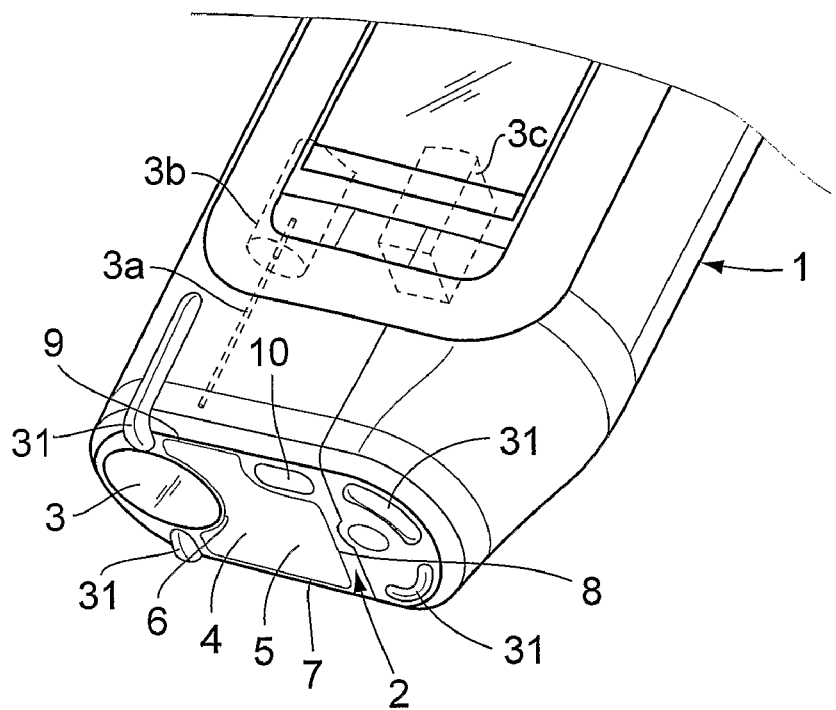
FIG. 1 is a partial perspective view of the outside of a medication injection device according to the invention, some internal components of the injection device being however diagrammatically and partially shown in dotted lines.

FIG. 1 shows the housing 1 of a medication injection device according to the invention. A bottom wall 2 of the housing 1 comprises a through hole 3 permitting passage of a needle 3a. The needle 3a is connected to a medication container 3b inside the housing 1. A mechanism 3c, including an electric motor, is also provided inside the housing 1 for holding and moving vertically the medication container 3b with its needle 3a so that these elements 3a, 3b can take a retracted position, fully inside the housing 1, and an operating position in which the needle 3a protrudes from the through hole 3 to pierce the skin of a patient. More details of the elements 3a, 3b, 3c may be found in WO 2005/077441.

In a central portion of the bottom wall 2, adjacent to the through hole 3, a second through hole is closed by an electrically insulating element 4 in the form of a plastic foil bonded to the external surface of the bottom wall 2. The external surfaces of the plastic foil 4 and of the bottom wall 2 define together a substantially flat contact surface 5 intended to touch the patient's skin. The plastic foil 4 has a concave side 6 and three straight sides 7, 8, 9. The concave side 6 is adjacent to the through hole 3 and follows part of the contour of that through hole 3. The straight sides 7, 8 define together a corner. The corner defined by the straight sides 8, 9 is truncated so as to leave room for an infrared emitter/receiver 10 provided for data transmission between the injection device and a computer.

Figure 2:
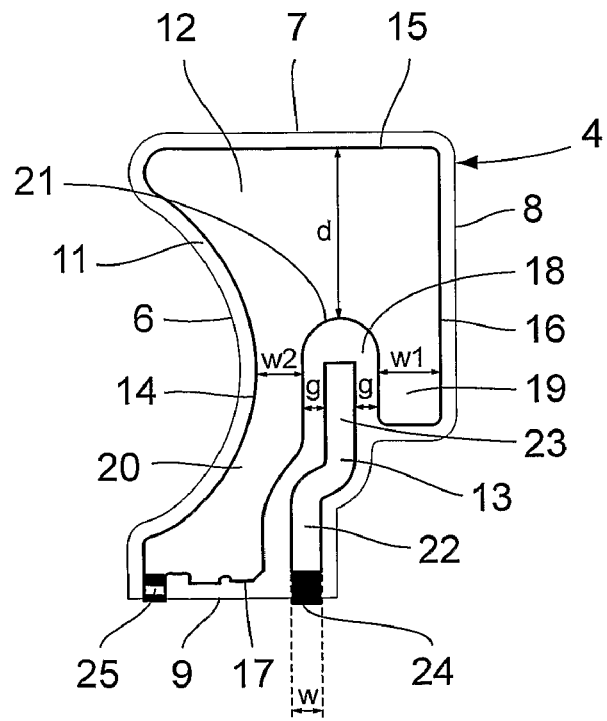
FIG. 2 is a top view of two electrodes of a capacitive proximity sensor included in the injection device according to the invention.

Referring now to FIG. 2, the plastic foil 4 (shown in thin lines on FIG. 2) supports on its internal surface 11 two coplanar metallic electrodes 12, 13 of a capacitive proximity sensor. The two electrodes 12, 13 are bonded to the internal surface 11 of the plastic foil 4 and define a plane that is parallel to the plastic foil 4. One, 12, of the electrodes 12, 13 is much larger than the other electrode 13, i.e. takes up a much larger area in the aforesaid plane. This larger electrode 12 is slightly smaller than the plastic foil 4 and comprises a concave side 14 and three straight sides 15, 16, 17 that correspond and are parallel respectively to the sides 6-9 of the plastic foil 4. The larger electrode 12 further defines a U-shaped recess 18 between the concave side 14 and its opposite straight side 16. The smaller electrode 13 has an elongate shape, and is disposed within the U-shaped recess 18, in a substantially parallel direction to the legs 19, 20 of the first electrode 12 formed by the U-shaped recess 18. The width w1, w2 of the legs 19, 20 and the distance d between the bottom 21 of the U-shaped recess 18 and the side 15 of the larger electrode 12 opposite said bottom 21 are larger than the width w of the second electrode 13. To leave room for the infrared emitter/receiver 10, the leg 19 corresponding to the side 16 of the larger electrode 12 is shorter than the leg 20 corresponding to the concave side 14 and a first straight portion 22 of the smaller electrode 13 that is remote from the bottom 21 of the U-shaped recess 18 is offset to the concave side 14 relative to a second straight portion 23 of the smaller electrode 13 that is close to the bottom 21 of the U-shaped recess 18. An electrical contact 24 is connected to the smaller electrode 13, at the end of the smaller electrode 13 that is remote from the bottom 21 of the U-shaped recess 18. Another electrical contact 25 is connected to the larger electrode 12, at the side 17 thereof.

Figure 3:
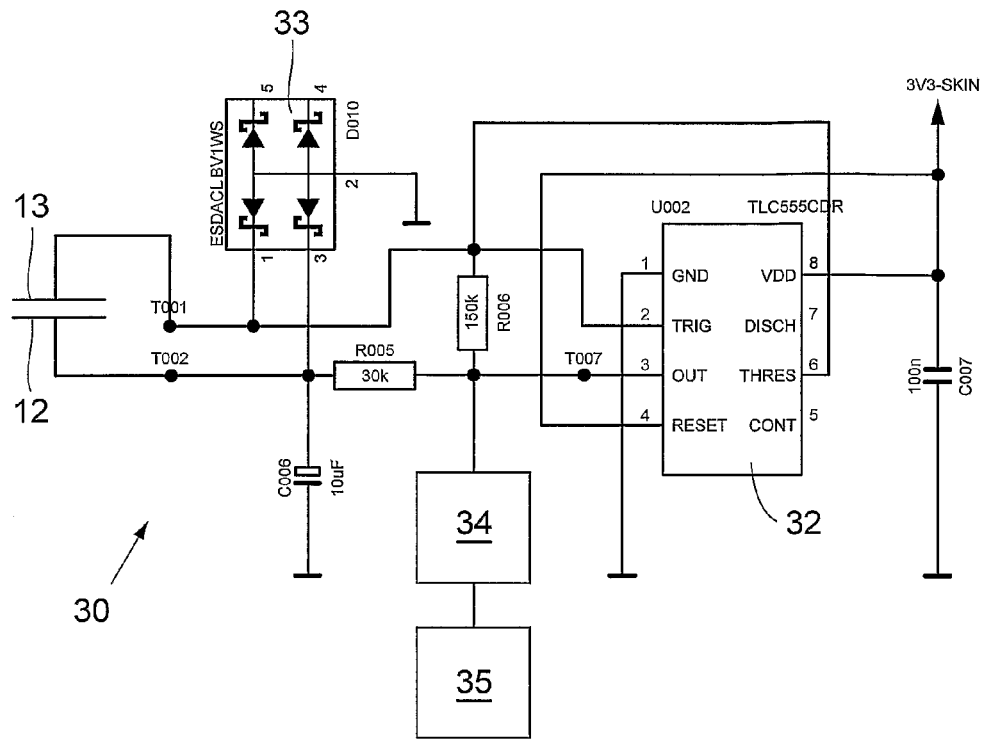
FIG. 3 is a diagram of an electronic circuit to which the electrodes shown in FIG. 2 are connected.

Referring to FIG. 3, the two electrodes 12, 13 are each connected via the electrical contacts 25, 24 to an electronic circuit 30 of the capacitive proximity sensor, provided inside the housing 1 of the injection device. The electronic circuit 30 is designed so that the two electrodes 12, 13 define together a capacitance and so that a change in said capacitance caused by an approaching human body is detected. Thanks to the shape and size of the electrodes 12, 13, and notably to the fact that the larger electrode 12 surrounds the smaller electrode 13 in the area of the U-shaped recess 18, the electric field between the electrodes 12, 13 is so shaped that it can be easily influenced from the outside of the sensor, in particular by human tissue. When human tissue approaches the electrodes 12, 13, the permittivity seen by the electric field is modified, because human tissue has a different permittivity than air. This results in a change of the capacitance defined by the electrodes 12, 13. The large size of the larger electrode 12, which is the measurement electrode (the smaller electrode 13 being a reference electrode), further increases the sensitivity of the sensor. The sensitivity of the sensor is still further increased by the small lateral gap g between the electrodes 12, 13, which is preferably less than the width w of the smaller electrode 13. Moreover, thanks to its concave side 14 which follows the contour of the through hole 3, the larger electrode 12 may be disposed very close to the hole 3 and the sensor may thus more accurately detect a proper positioning of the injection device on the patient's skin area which is to be pierced by the needle 3a.

In practice, the sensor is so set to detect a change in the capacitance defined by the electrodes 12, 13 when a sufficient volume of human tissue has entered the electric field generated by the electrodes 12, 13. The said sufficient volume of human tissue can be so determined, for example, that a mere contact of a finger, in particular a child finger, with the external surface of the plastic foil 4 of the injection device, opposite the electrodes 12, 13, does not activate the sensor whereas a contact of the area of the patient's skin where the injection is to be performed, for example an arm, does activate the sensor. Another condition fulfilled by the sensor can be that materials such as wood, plastic, glass, metal, ceramic, particularly in dry (i.e. not wet) condition, as well as dry textile (dry cotton) and dry leather do not activate the sensor when they are brought into contact with the plastic foil 4. In particular, the setting can be such that human skin is not detected through dry clothes. To facilitate discriminating between human skin and other materials, the bottom wall 2 of the injection device has feet 31 (see FIG. 1) for preventing contact of the skin contact surface 5 with flat rigid surfaces such as tables, etc., while allowing contact of the skin contact surface 5 with soft objects such as human skin. The feet 31 permits also reducing environmental influences of metallic surfaces, e.g. copper, iron.

Activation of the sensor causes a control unit in the injection device to allow the injection of one dose of medication into the patient after an injection button has been pressed by the patient. With the above settings, the sensor according to the invention improves the patient's safety since the sensor is activated and the injection is allowed only when the injection device is properly placed on the patient's skin. Placing the device on an unsuitable area, such as on clothes or on a hard surface, will not activate the sensor and, therefore, operating the injection button will not cause medication to be expelled out of the device. More particularly, operating the injection button in a condition where the sensor is not activated will not cause the needle 3a to be moved out of the through hole 3. This avoids breaking the needle 3a by moving it out while the injection device is placed on a hard surface such as a table surface or accidentally piercing the user's skin while the injection device is being handled.

As shown in FIG. 3, the electronic circuit 30 of the sensor comprises, according to a preferred embodiment, a timer circuit 32 commercially available under reference Texas Instrument TLC555CDR and configured to deliver a periodic signal at its output OUT. The larger electrode 12 is connected to the output OUT of the timer circuit 32 via a resistor R005 of 30 kΩ, and therefore receives the periodic signal via said resistor. The smaller electrode 13 is directly connected to the triggering input TRIG and the threshold input THRES of the timer circuit 32. The inputs VDD and RESET of the timer circuit 32 are connected to a fixed voltage of 3.3 V. A capacitor C007 of 100 nF has a first terminal connected to ground and a second terminal connected to the inputs VDD and RESET of the timer circuit 32. A resistor R006 of 150 kΩ has a first terminal connected to the output OUT of the timer circuit 32 and to a first terminal of the resistor R005, and a second terminal connected to the smaller electrode 13 and to the inputs TRIG and THRES of the timer circuit 32. A capacitor C006 of 10 pF has a first terminal connected to ground and a second terminal connected to the second terminal of resistor R005 and to the larger electrode 12. A Zener diode circuit 33 is also provided for electrostatic discharge (ESD) protection.

In the electronic circuit as shown in FIG. 3, the frequency of the periodic signal output by the timer circuit 32 depends on the capacitance formed by the two electrodes 12, 13. When human tissue enters the electric field generated by the electrodes 12,13, the capacitance formed by the electrodes 12, 13 is changed, which results in a change of the frequency of the periodic signal. A processor 34 connected to the output OUT of the timer circuit 32 detects when the frequency is below a preselected threshold. Detection of a frequency below the preselected threshold corresponds to an activation of the sensor, i.e. to a detection of the proximity of an object. Activation of the sensor followed by operation of the injection button causes a control unit 35 to control the mechanism 3c so that the medication container 3b with the needle 3a is moved down to its operating position and then to control movement of a piston of the medication container 3b through another mechanism (not shown) for expelling medication and thus performing the injection.

Figure 4:
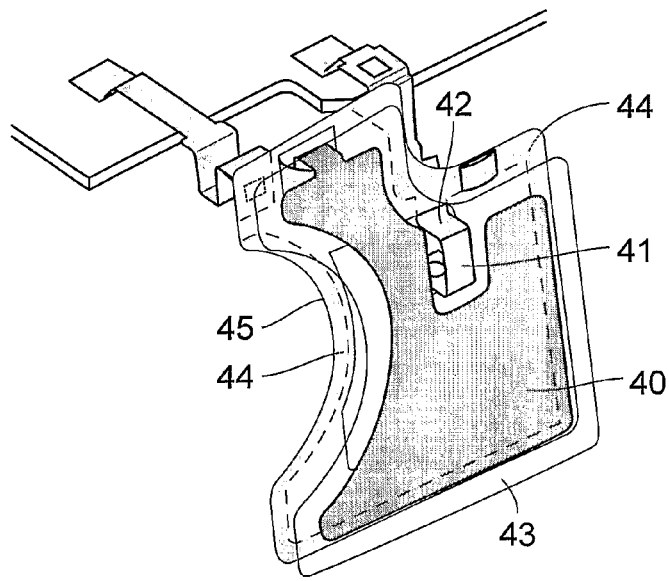
FIG. 4 is a perspective view showing three electrodes of an alternate embodiment of the capacitive proximity sensor included in the injection device according to the invention.

Referring to FIG. 4, a capacitive proximity sensor used in an alternate embodiment of the invention comprises a large, measurement electrode 40 and a small, reference electrode 41. The measurement electrode 40 has the same shape as the electrode 12 shown in FIG. 2. The reference electrode 41 is formed by a flat rectangular portion of a bent metal strip 42, and is coplanar with and surrounded by the measurement electrode 40. The measurement and reference electrodes 40, 41 are protected by a plastic foil 43, like in the embodiment of FIG. 2. Besides the electrodes 40, 41, the sensor used in this alternate embodiment comprises a third, compensation electrode 44. The compensation electrode 44 is disposed in a plane parallel to the plane defined by the measurement and reference electrodes 40, 41, at a certain distance from the electrodes 40, 41, and is connected to the reference electrode 41. Practically, the compensation electrode 44 is disposed on the inner surface of a second foil 45 that is parallel to the foil 43 and located on the inner side of the foil 43. The shape of the compensation electrode 44 substantially corresponds to the contour of the measurement electrode 40.

The purpose of the compensation electrode 44 is to limit the electric field of the capacitive proximity sensor to the area where the skin detection should take place. The compensation electrode 44 thus prevents that handling the injection device, i.e. holding the injection device with hands, be detected as a proper placement of the device onto human skin. The compensation electrode 44 also shields the electric field. This is important for injection devices that are powered with batteries.

The invention claimed is:

1. Injection device for injecting medication to a patient, comprising a surface having a through hole for passage of a needle, further comprising a capacitive proximity sensor for detecting proximity or contact of human skin to/with said surface, said capacitive proximity sensor including a first electrode, a second electrode defining a capacitance with the first electrode and means for detecting a change in said capacitance due to the proximity of human skin to the sensor, and further comprising a compensation electrode for limiting the electric field generated by the first and second electrodes to a determined area.

2. Injection device according to claim 1, further comprising a control unit which allows injection of medication only when detection by the sensor occurs.

3. Injection device according to claim 2, further comprising a mechanism for moving the needle between a retracted position, inside the device, and an operating position, in which the needle protrudes from the through hole, said control unit allowing the mechanism to move the needle from the retracted position to the operating position only when detection by the sensor occurs.

4. Injection device according to claim 1, wherein said capacitive proximity sensor is so set that detection occurs when a sufficient volume of human tissue has entered an electric field generated by the capacitive proximity sensor, a mere contact of a finger on said surface not being sufficient for the detection to occur.

5. Injection device according to claim 1, wherein said capacitive proximity sensor is so set to substantially not detect dry clothes.

6. Injection device according to claim 1, wherein said capacitive proximity sensor is so set to substantially not detect any of the following materials: dry cotton, dry leather.

7. Injection device according to claim 1, wherein said capacitive proximity sensor is so set to substantially not detect any of the following materials: wood, plastic, metal, ceramic, glass.

8. Injection device according to claim 1, wherein feet are provided on said surface to prevent contact of said surface with a rigid surface while permitting contact of said surface with human skin.

9. Injection device according to claim 1, wherein said capacitive proximity sensor is adjacent to said through hole.

10. Injection device according to claim 1, wherein the first and second electrodes are substantially coplanar and disposed in a plane parallel to said surface.

11. Injection device according to claim 10, wherein said first and second electrodes are disposed on an internal surface of an insulating element, said insulating element having an external surface which defines at least part of said surface having said through hole.

12. Injection device according to claim 1, wherein the first electrode surrounds, at least partly, the second electrode.

13. Injection device according to claim 12, wherein the second electrode has an elongate shape.

14. Injection device according to claim 13, wherein the second electrode is disposed within a U-shaped recess defined by the first electrode and is substantially parallel to the legs of the first electrode formed by the U-shaped recess.

15. Injection device according to claim 14, wherein the width (w1, w2) of said legs and the distance (d) between the bottom of the U-shaped recess and a side of the first electrode opposite said bottom are larger than the width (w) of the second electrode.

16. Injection device according to claim 13, wherein a lateral gap (g) between the first and second electrodes is smaller than the width (w) of the second electrode.

17. Injection device according to claim 12, wherein the first electrode is larger than the second electrode.

18. Injection device according to claim 1, wherein one side of the first electrode is adjacent to the through hole and has a concave shape that follows part of the contour of the through hole.

19. Injection device according to claim 1, wherein said means for detecting a change in said capacitance comprises a first electronic circuit which delivers a periodic signal to the first electrode.

20. Injection device according to claim 19, wherein the first electronic circuit is a timer circuit having an output connected to the first electrode, a triggering input and a threshold input, the triggering and threshold inputs being both connected to the second electrode.

21. Injection device according to claim 19, wherein the frequency of the periodic signal depends on said capacitance, and in that said means for detecting a change in said capacitance further comprises a second electronic circuit for detecting a change in said frequency due to the proximity of human skin to the sensor.

22. Injection device according to claim 1, wherein the compensation electrode is disposed in a plane parallel to a plane defined by the first and second electrodes, is connected to the second electrode, and has a shape which substantially corresponds to the contour of the first electrode.

* * * * *